(12) United States Patent
Marino

(10) Patent No.: US 11,771,500 B2
(45) Date of Patent: Oct. 3, 2023

(54) SURGICAL NAVIGATION USING A GUIDE FOR INSTRUMENTATION POSITIONING

(71) Applicant: HipNav Technologies, LLC, San Diego, CA (US)

(72) Inventor: James F. Marino, La Jolla, CA (US)

(*) Notice: Subject to any disclaimer, the term of this patent is extended or adjusted under 35 U.S.C. 154(b) by 810 days.

(21) Appl. No.: 16/295,249

(22) Filed: Mar. 7, 2019

(65) Prior Publication Data
US 2019/0298455 A1 Oct. 3, 2019

Related U.S. Application Data

(60) Provisional application No. 62/639,835, filed on Mar. 7, 2018.

(51) Int. Cl.
| | |
|---|---|
| *A61B 34/20* | (2016.01) |
| *A61B 17/88* | (2006.01) |
| *A61F 2/36* | (2006.01) |
| *A61F 2/46* | (2006.01) |
| *A61B 90/00* | (2016.01) |
| *A61B 17/00* | (2006.01) |

(Continued)

(52) U.S. Cl.
CPC ............. *A61B 34/20* (2016.02); *A61B 17/88* (2013.01); *A61B 90/06* (2016.02); *A61F 2/36* (2013.01); *A61F 2/4607* (2013.01); *A61B 17/1746* (2013.01); *A61B 2017/00221* (2013.01); *A61B 2017/564* (2013.01); *A61B 2034/2048* (2016.02); *A61B 2034/2051* (2016.02); *A61B 2090/061* (2016.02); *A61B 2090/363* (2016.02); *A61B 2090/3991* (2016.02); *A61F 2002/4658* (2013.01)

(58) Field of Classification Search
CPC ......... A61B 90/10; A61B 90/06; A61B 90/11; A61B 17/1746; A61B 34/10; A61B 34/20; A61B 34/25; A61B 2034/2048; A61B 2034/2051; A61B 2034/2046; A61B 2034/2068; A61B 2034/2074; A61B 2034/252; A61B 2034/254; A61B 2017/564; A61B 2090/061; A61B 2090/3937; A61B 2090/3991; A61B 2090/363; A61B 2560/0223; A61B 2560/0487; A61B 5/064; A61B 2017/00221; A61B 17/1742; A61B 17/88; A61B 17/8841; A61B 2034/20; A61B 2034/68; A61F 2002/4658; A61F 2002/4681; A61F 2/4607; A61F 2/36
USPC ....................................................... 606/102
See application file for complete search history.

(56) References Cited

U.S. PATENT DOCUMENTS

| | | | | |
|---|---|---|---|---|
| 5,141,512 | A * | 8/1992 | Farmer .................. | A61F 2/4657 606/89 |
| 8,974,468 | B2 * | 3/2015 | Borja .................... | A61B 5/1077 606/102 |

(Continued)

*Primary Examiner* — Marcela I. Shirsat
(74) *Attorney, Agent, or Firm* — Mintz Levin Cohn Ferris Glovsky and Popeo, P.C.

(57) ABSTRACT

The disclosed devices and methods relate to fixing (i.e., positioning) a multiaxial reference sensor (e.g., inclinometer(s) and compass sensor) or a mechanical guide to the skeletal anatomy in a known orientation, and then utilizing this reference sensor or mechanical guide to position instrumentation and/or implants with a second multiaxial positioning sensor or via a guide rod that provides spatial positioning information relative to the reference sensor or skeletally fixed references.

12 Claims, 29 Drawing Sheets

(51) Int. Cl.
*A61B 17/56* (2006.01)
*A61B 17/17* (2006.01)

(56) References Cited

U.S. PATENT DOCUMENTS

| | | | | |
|---|---|---|---|---|
| 2004/0210233 | A1* | 10/2004 | Yoon | A61F 2/4609 |
| | | | | 606/102 |
| 2005/0033117 | A1* | 2/2005 | Ozaki | A61B 5/062 |
| | | | | 600/109 |
| 2005/0203540 | A1* | 9/2005 | Broyles | A61B 17/1742 |
| | | | | 606/102 |
| 2009/0171370 | A1* | 7/2009 | Yoon | A61F 2/4609 |
| | | | | 606/130 |
| 2012/0157887 | A1* | 6/2012 | Fanson | A61F 2/32 |
| | | | | 600/595 |
| 2014/0039565 | A1* | 2/2014 | Martineau | A61B 17/866 |
| | | | | 606/304 |
| 2015/0182292 | A1* | 7/2015 | Hladio | A61B 90/06 |
| | | | | 606/87 |
| 2016/0135900 | A1* | 5/2016 | Falardeau | A61B 34/20 |
| | | | | 600/424 |

* cited by examiner

1605

SURGICAL NAVIGATION USING A GUIDE FOR INSTRUMENTATION POSITIONING

CROSS REFERENCE TO RELATED APPLICATION

This application claims priority of co pending U.S. Provisional Patent Application Ser. No. 62/639,835 filed on Mar. 7, 2018. Priority of the aforementioned filing date is hereby claimed and the disclosure of the provisional patent application is hereby incorporated by reference in its entirety.

BACKGROUND

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

Surgical procedures requiring high precision of instrumentation and/or implant placement are increasingly performed with the aid of various surgical navigation devices. Some of these devices utilize computer generated three-dimensional (3-D) modeling of relevant anatomy combined with intraoperative radiologic or electromechanical (infrared or radiofrequency) registration (i.e., fiduciaries), to locate the relevant anatomy in space. While these systems may be versatile, they often require expensive and potentially harmful (e.g., ionizing irradiation from CT scans) imaging studies, as well as placing significant intraoperative demands for registration.

A goal for surgical navigation is to spatially position instrumentation and/or implants accurately with respect to certain anatomy of the patient (e.g., acetabular component of a hip replacement procedure within the acetabular socket). At times, the relevant anatomy can be oriented in space based upon surface landmarks that might be accessible via direct or indirect inspection and/or palpation of the patient (e.g., the anterior superior iliac spines and the symphysis pubis, defining the anterior pelvic plane). At other times, an instrument can be placed on or within the skeletal anatomy (e.g., intramedullary rod with condylar referencing) to provide skeletal spatial positioning.

Thus, tools and techniques to assist in the accurate placement of instrumentation and/or implants are desired.

SUMMARY

Aspects of the current subject matter relate to surgical navigation tools and techniques. Aspects of the current subject matter allow for assessment of soft tissue depth beneath stanchions of an anterior pelvic frame, allowing for adjustment of the frame to optimize pin/screw placement in the hemi-pelvis in a manner that accurately correlates with the boney anatomy that defines the anterior pelvic plane.

Additional aspects relate to a defined specific relationship between two skeletally fixed pins/screws to the hemi-pelvis and the anterior pelvic frame. Utilizing two screws with this specific spatial relationship provides a method of referencing the anterior pelvic plane, as well as determining limb length and trochanteric offset. Additional aspects provide controlled acetabular depth and orientation of reaming with the aid of the pins/screws fixed in a spatially known relationship to the anterior pelvic frame.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of the specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

While there are various existing means of utilizing surgical navigation, generally with computer assistance (e.g., computer assisted surgery (CAS) or robotic navigation), these have had sufficient detractions in cost, effectiveness, and/or convenience to limit their utilization and utility. The disclosed devices and methods overcome at least some of these detractions, by utilizing relatively low cost means (wireless communicating multiaxial inclinometers and compass MEM sensors and/or mechanical surgical guides and surgical guide rods engaged) of spatially referencing relevant skeletal anatomy relative to instrumentation used to fashion bone or position implants, for example.

The disclosed devices and methods relate to fixing (i.e., positioning) a multiaxial reference sensor (e.g., inclinometer(s) and compass sensor) or a mechanical guide to the skeletal anatomy in a known orientation, and then utilizing this reference sensor or mechanical guide to position instrumentation and/or implants with a second multiaxial positioning sensor or via a guide rod that provides spatial positioning information relative to the reference sensor or skeletally fixed references.

For example, in performing hip replacement surgery, it is highly desirable to orient the acetabular component in a specific manner that optimizes subsequent implant stability, limb strength, limb length, and implant surface wear. The most common method for ascertaining this is based upon surgeon experience and the use of skeletal (e.g., acetabular rim) and soft tissue (e.g., transverse acetabular ligament) landmarks. While this method can be very accurate in general, there remains a small but significant percentage of patients who will have implants positioned sub-optimally, leading to higher rates of dislocation, implant impingement, relative weakness of the limb musculature, increased implant surface wear rates, and symptomatic limb length inequalities.

Figure 1A:
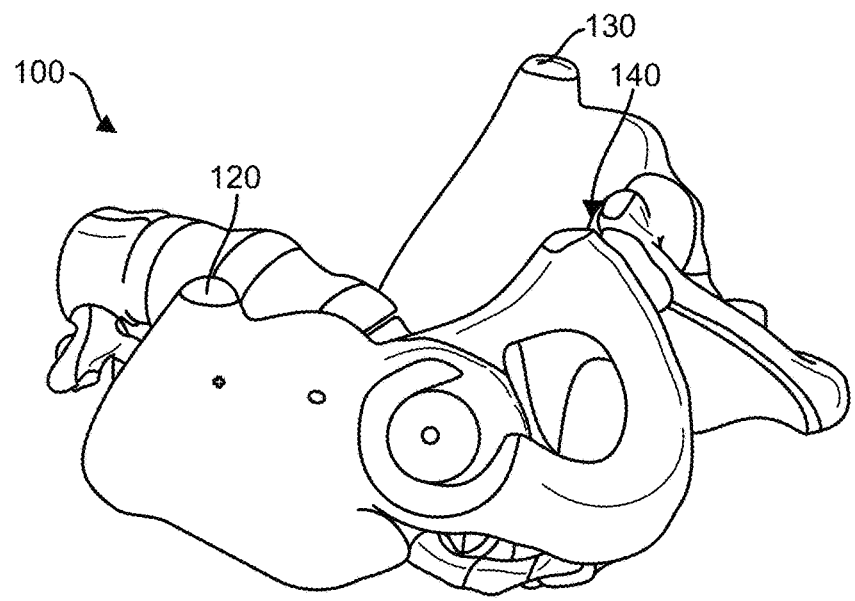
FIGS. 1A-1D, 2, 3, 4A-4B, 5A-5B, 6A-6B, 7A-7D, and 8 illustrate various features of a frame, a reference sensor, a positioning sensor, and a mechanical drill guide consistent with implementations of the current subject matter.
Figure 1B:
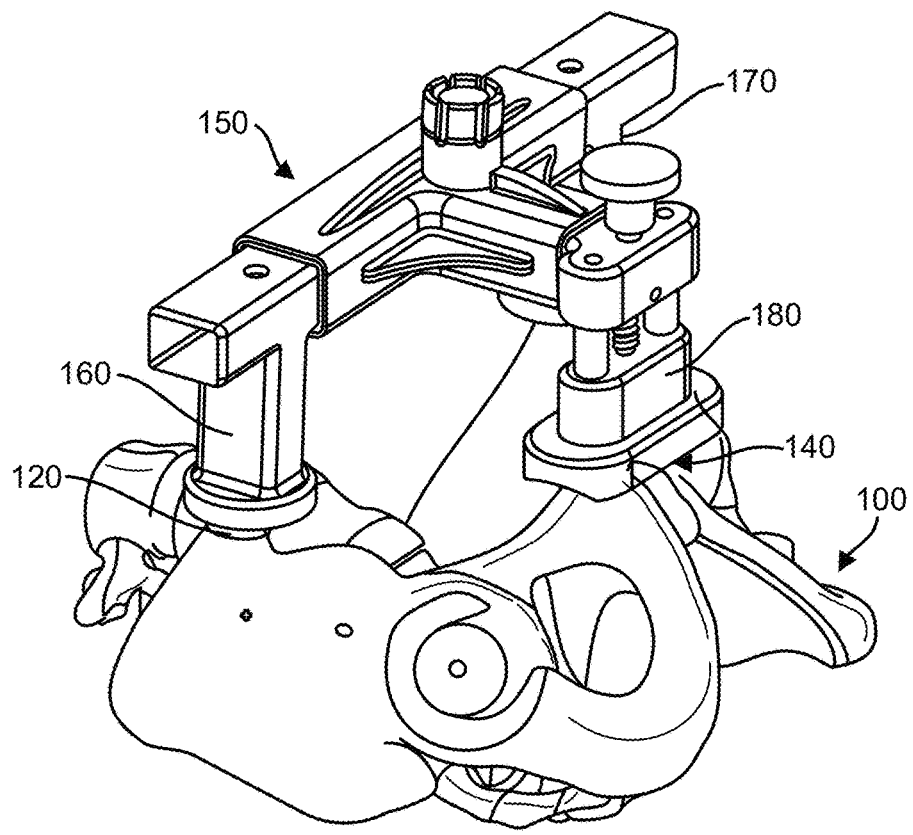

FIG. 1A illustrates a pelvis 100 of a supine patient indicating the anterior superior iliac spine (ASIS) prominences 120,130 and the symphysis pubis (SP) 140. With reference to FIG. 1B, in accordance with an embodiment, a three-legged frame 150 is positioned over the pelvis 100 of the supine patient, with each of two legs 160,170 resting on the cutaneous surfaces immediately superficial to the anterior superior iliac spine (ASIS) prominences 120,130, while a third leg 180 is supported by the skin and subcutaneous tissue immediately superficial to the symphysis pubis (SP) 140. The frame 150 is configured to maintain the distance from each ASIS to the SP, equidistant.

Figure 1C:
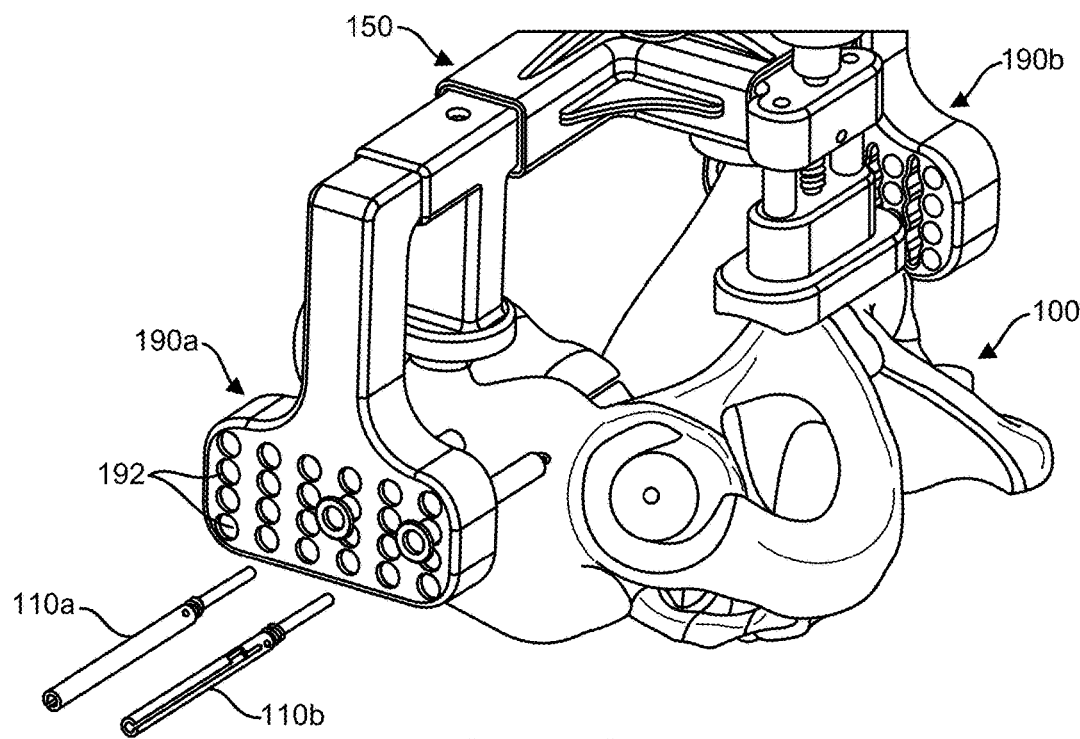

As shown in FIG. 1C, one or more adjustable surgical guides 190a,190b are associated with the frame 150. The guides 190a, 190b are configured to position pins or screws (e.g., two pins 110a,110b, as shown in FIG. 1C) in the lateral pelvis superior to the acetabular cavity. The guides 190a, 190b may allow for additional pins or screws to be positioned. The guides 190a,190b comprise one or more guide holes or channels 192 for such positioning and placement.

Figure 1D:
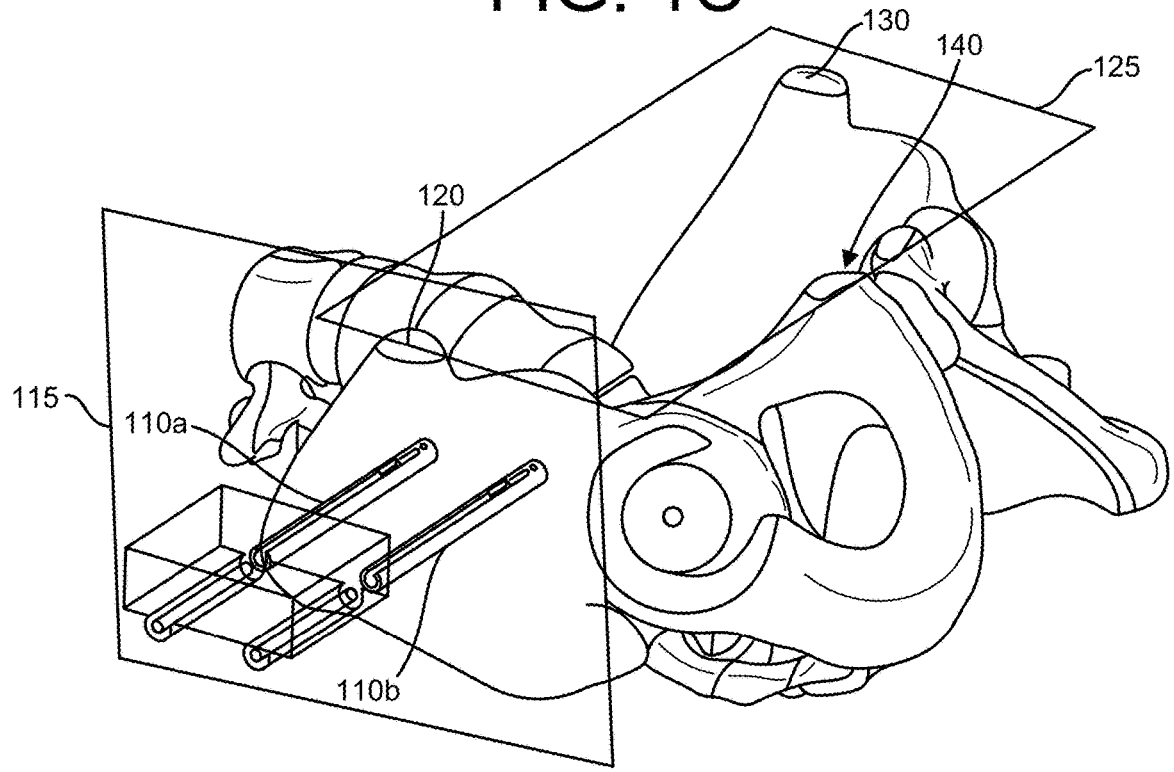

The two specialized pins/screws 110a,110b are placed into the lateral aspect of the pelvis above the acetabular fossa (as shown in FIG. 1C). These pins/screws 110a,110b are inserted along axes that are each parallel with a line defined by both anterior superior iliac spine (ASIS) prominences 120,130. As shown in FIG. 1D, a plane 115 that contains bone pins/screws' axes is parallel with a plane defined by both ASISs 120,130 and the SP 140 or is referenced to the anterior pelvic plane 125 (defined by the symphysis pubis (pubic tubercles) 140 and both ASISs 120,130).

Figure 2:
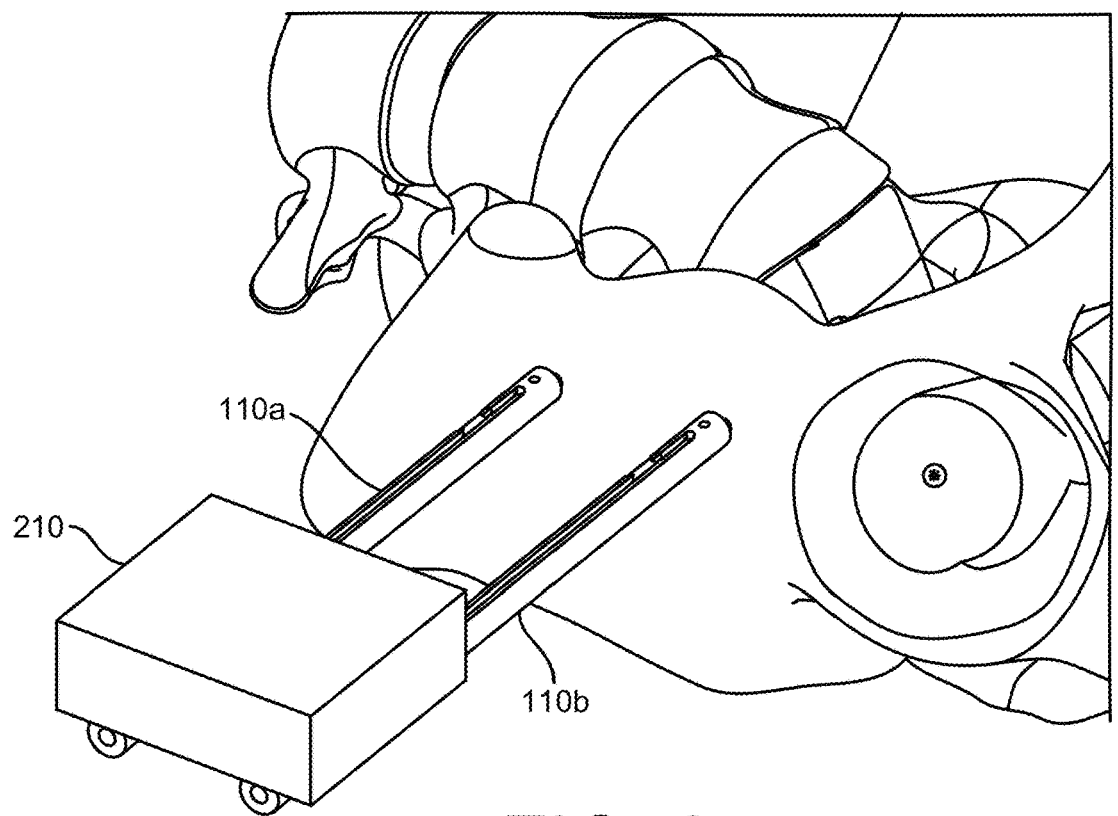
Figure 3:
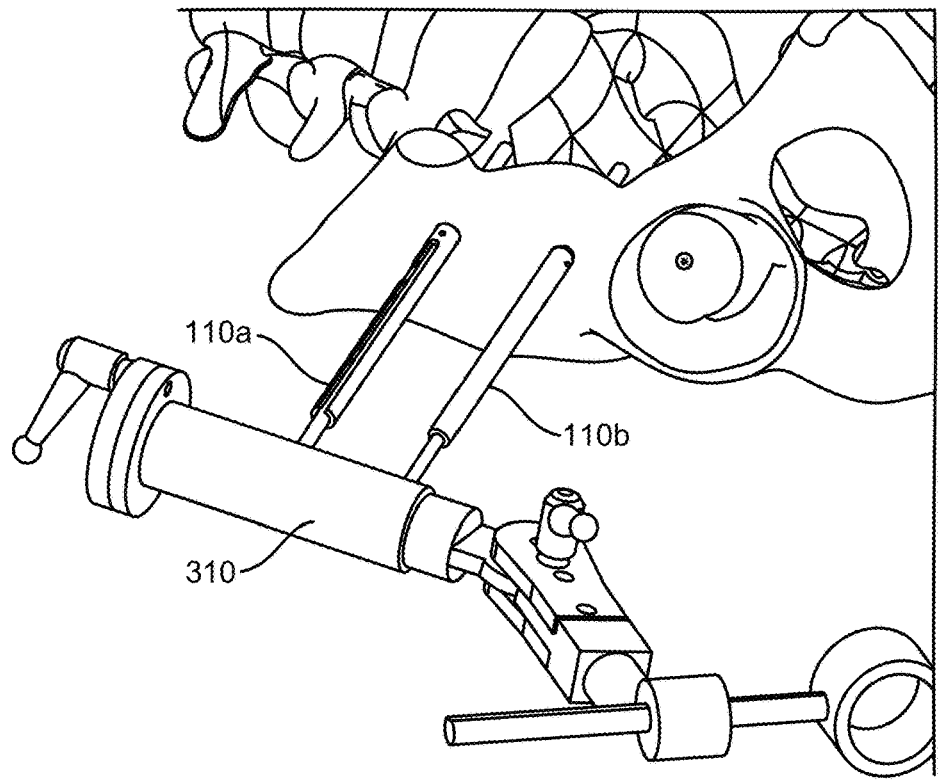

Now with reference to FIG. 2, a first multiaxial sensor 210 (i.e., a reference sensor) is attached to the two pins/screws 110a,110b, such that when the patient is placed on his or her side (positioned for surgery) the reference sensor 210 is located above the patient's pelvis 100. If the patient is positioned supine for the hip replacement procedure, the reference sensor 210 is positioned lateral to the respective operative hemi-pelvis. Alternatively, as shown in FIG. 3, a mechanical drill guide 310 or reamer/implant insertor guide rod may be temporarily associated with both pins/screws 110a,110b, to provide orientation for acetabular drilling, reaming, and implant insertion. As shown in FIG. 3, the drill guide 310 has an attached radially positioned ring configuration (attached via a connection component or structure) to visually position a drill within the acetabular socket of the patient.

As described above, the pins/screws 110a,110b are placed into the pelvis 100 such that a plane containing both of their axes is parallel (or angularly referenced) to the plane defined by the two ASISs 120,130 and the symphysis pubis 140 or anterior prominences of the pubic tubercles (i.e., the anterior pelvic plane). Each axis of the pin/screw 110a,110b is parallel to a line defined by both ASISs 120,130. Thus, the reference sensor 210, or mechanical drill guide and guide rod positioner 310, is positioned and secured to the patient's pelvis in a manner that relative orientation to the reference sensor 210, or to the mechanical drill guide and guide rod positioner 310, provides relative orientation to the pelvis (via their collective spatial reference to the anterior pelvic plane).

Figure 4A:
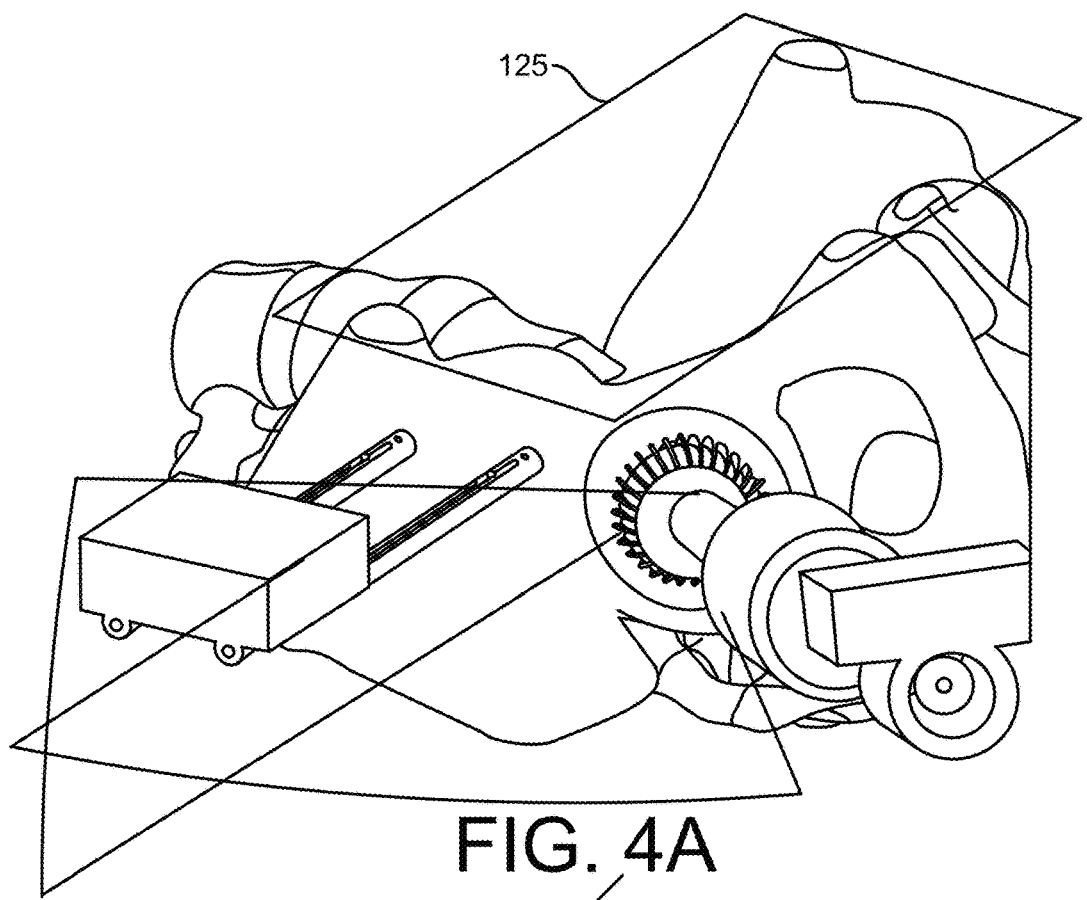
Figure 4B:
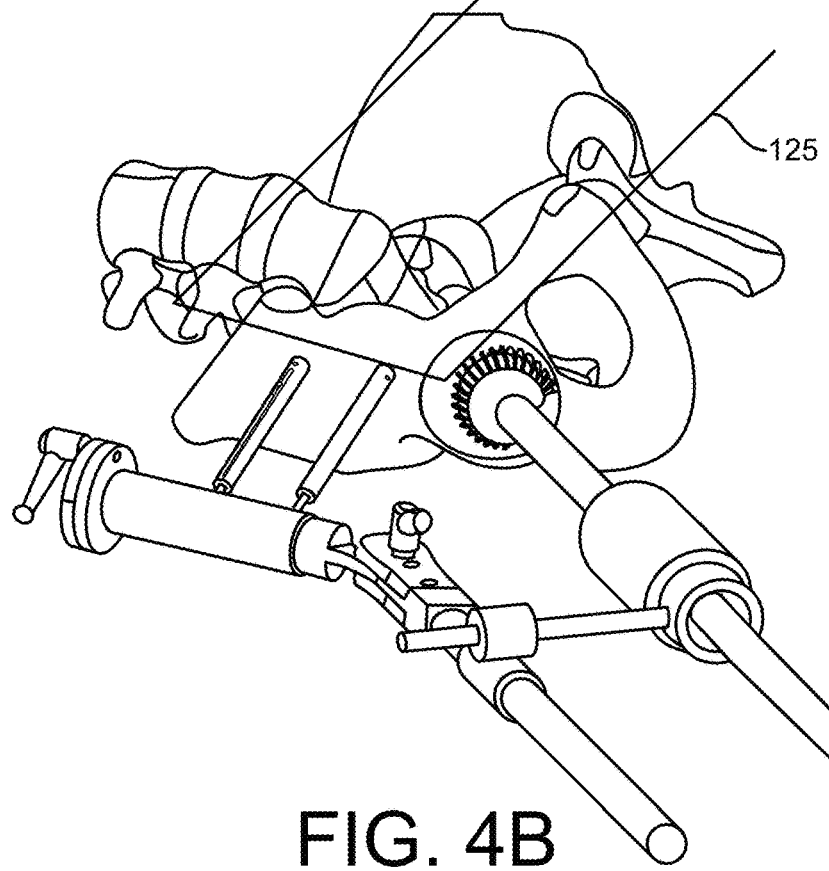

With reference to FIGS. 4A and 4B, reference abduction and anteversion values can be determined and/or recorded relative to a reference multiaxial sensor 210 or a fixed or adjustable mechanical drill/reamer/insertor guide 310 associated with the two screws/pins 110a,110b having axes oriented parallel to the anterior pelvic plane as well as parallel to a line defined by both ASISs 120,130. In a lateral decubitus position, an MEM sensor (i.e., inclinometer) records coronal plane pelvic tilt reference values determined by the angle subtended by the inclinometer relative to the gravitational vector within a plane parallel angularly referenced to the anterior pelvic plane (also parallel to a plane defined by the axes of the two pins/screws 110a,110b).

In this same lateral position, the reference anteversion values are recorded by an inclinometer sensor measuring within a plane that is orthogonally intersected by the sagittal plane or a plane. A third sensor (a heading or magnetic field sensor) is orthogonally oriented relative to the previous two MEM sensors, with possible utilization to adjust for axial plane tile variance relative to the sagittal plane (determined, for example, through the use of preoperative or intraoperative X-rays). The sensor is optional as there are no critical values to be determined in this plane. If the patient is positioned in the supine position, one of the inclinometer sensors will exchange functionality with the magnetic field or heading sensor.

With the multiaxial reference sensor 210 secured to the pelvis via two pins or screws 110a,110b and used to determine the orientation of the pelvis in space, use of a second multiaxial measurement sensor associated with the instrumentation used to fashion the pelvis (e.g., reamer shaft) or insert the acetabular implant (e.g., cup positioner shaft), enables the determination of relative spatial orientation (that is relative to the reference sensor 210) that provides for relatively precise and objective acetabular floor (i.e. foveal or cotyledon notch) drilling, acetabular reamer orientation, and implant position orientation, relative to the pelvic anatomy. Similarly, a mechanical drill guide/guide rod positioner 310 (fixed or adjustable) can be temporarily associated with the two pins/screws 110a,110b (fixed to the hemi pelvis), to provide for precisely directed drilling of the acetabular floor (to assess and control for acetabular reaming depth, reamer position-relative to the native acetabular socket, and reamer/implant orientation-relative to the anterior pelvic plane).

Figure 5A:
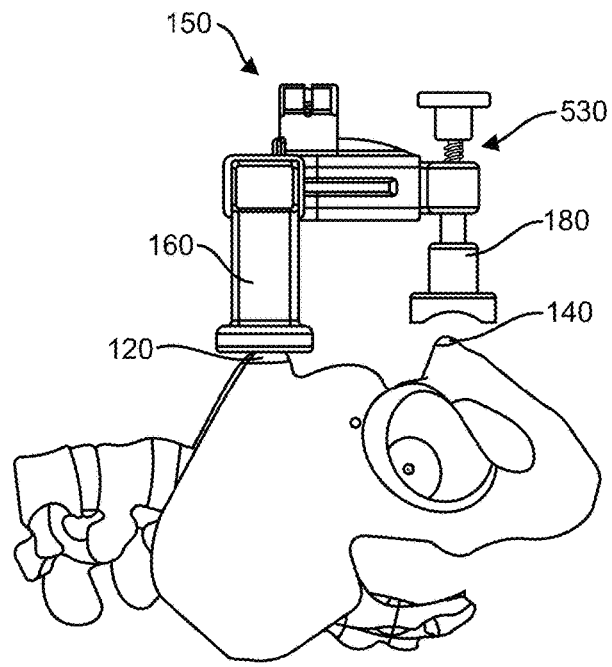
Figure 5B:
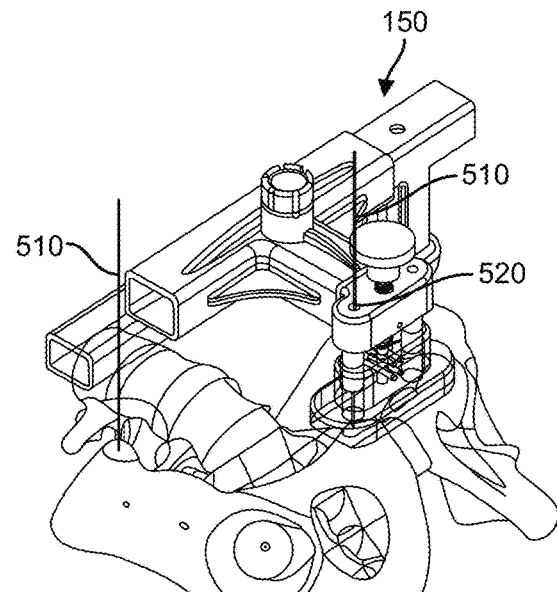
Figure 5B:
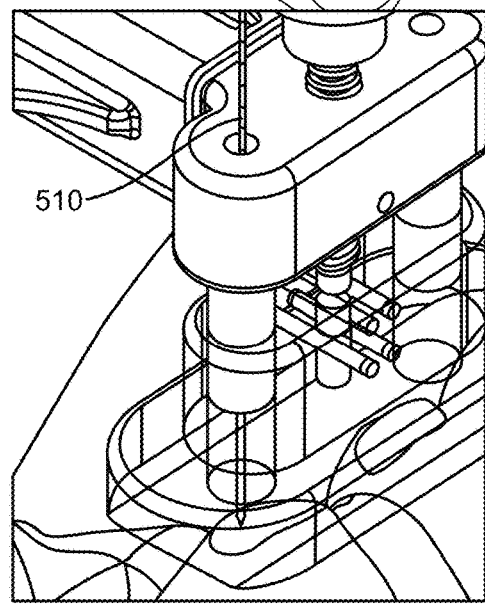

With reference to FIGS. 5A and 5B, with the patient in a supine position, and the operative (e.g., arthritic hip scheduled for replacement) positioned at the edge of the operative table (to allow the gluteal mass to fall posteriorly), the patient's anterior pelvic plane is determined by palpation of the subcutaneous boney landmarks (i.e., both ASISs 120,130 and the SP 140). An adherent localizing skin marker (e.g., EKG electrode or something similar) can be placed on the relaxed skin immediately over the boney prominence. These skin markers can be used to localize as well as stabilize the three supportive stanchions or legs 160,170,180 of the pelvic frame 150. Alternatively, the stanchions 160,170,180 can rest on the surface anatomy with conforming surface features to reduce the risk of frame migration. Measurement of the soft tissue depth (i.e., the distance from the skin surface immediately below the stanchions or legs 160,170,180 to the underlying bone) superficial to one or each ASIS 120,130 and the pubic tubercle(s), is accomplished with the use of one or more pin depth probes 510 (e.g. measured from the top of each stanchion 160,170,180 to the superficial underlying bone) or via a non-invasive ultrasound diagnostic measurement tool. This can be accomplished via a relatively small notch or aperture/channel 520 in the stanchions. The disparity in soft tissue depth associated with the stanchion supports can be accommodated via an adjustment in height of one or several of the stanchions 160,170,180 (it is anticipated that the soft tissue depth associated with both ASISs will be similar and the disparity between the soft tissue depth associated with the pubic tubercle stanchion and the ASIS stanchions will be of greater clinical concern). In an embodiment, a single height adjustment component 530 is provided to adjust the height of the symphysis pubis stanchion 180, to accommodate for this variance in soft tissue depth that can lead to inaccuracies of representation of the anterior pelvic plane.

The pelvic frame 150 is positioned over the respective boney landmarks of the ASISs 120,130 and the symphysis pubis (pubic tubercles) 140. This can be accomplished in a supine position or in the lateral decubitus position. Compression of the frame 150 against the patient is accomplished via, for example, an attachment to the operative table rail to either compress the pelvis against the operative table padding (i.e. supine position) or against a sacral support pad (i.e. lateral decubitus positioning). A spring loaded compression mechanism can be integral to the pelvic frame positioner. A generous area of skin immediately adjacent and superior to the operative side greater trochanter is prepped with a rapid acting antiseptic skin preparation and field towels used to isolate the area from adjacent regions. A sterile-gloved or gloved and gowned surgeon then secures the pin/screw guide 190a,190b to a track on the operative side and then slides the pin guide 190a,190b along the track until the pin guide 190a,190b is adjacent to the proximal lateral thigh and pelvis. Adjustments for the position of the frame 150 and the attached drill/pin/screw guide 190a,190b can be secured with friction locks or the like. Small stab incisions are made into the skin a prescribed distance above the greater trochanter (e.g., two finger breadths), and two pins or screws 110a,110b are advanced into the pelvis along the axes defined by the sterile guide 190a,190b, with or without the aid of a sharp drill or trocar tip to create cortical holes aligned with the pin guides channels 192.

The pins or screws 110a,110b are then advanced into the pelvis such that they are secured to both the lateral and the medial wall of the ilium, with axes parallel to both the anterior pelvic plane and a line segment defined by both ASISs 120,130. The pins or screws 110a,110b may reside essentially flush with or sub-flush with the soft tissue mass of the lateral pelvis. A skin sterile barrier may then be placed over the pin/screw tract wounds and the patient may then be positioned and secured as would normally occur for a hip replacement procedure (i.e., generally in the lateral decubitus position with the operative side up), unless the pelvic frame itself is being used with appropriate padding attachments for lateral decubitus positioning. Standard preparation and draping would ensue (adherent skin sterile barrier removed before or after this effort).

Figure 6A:
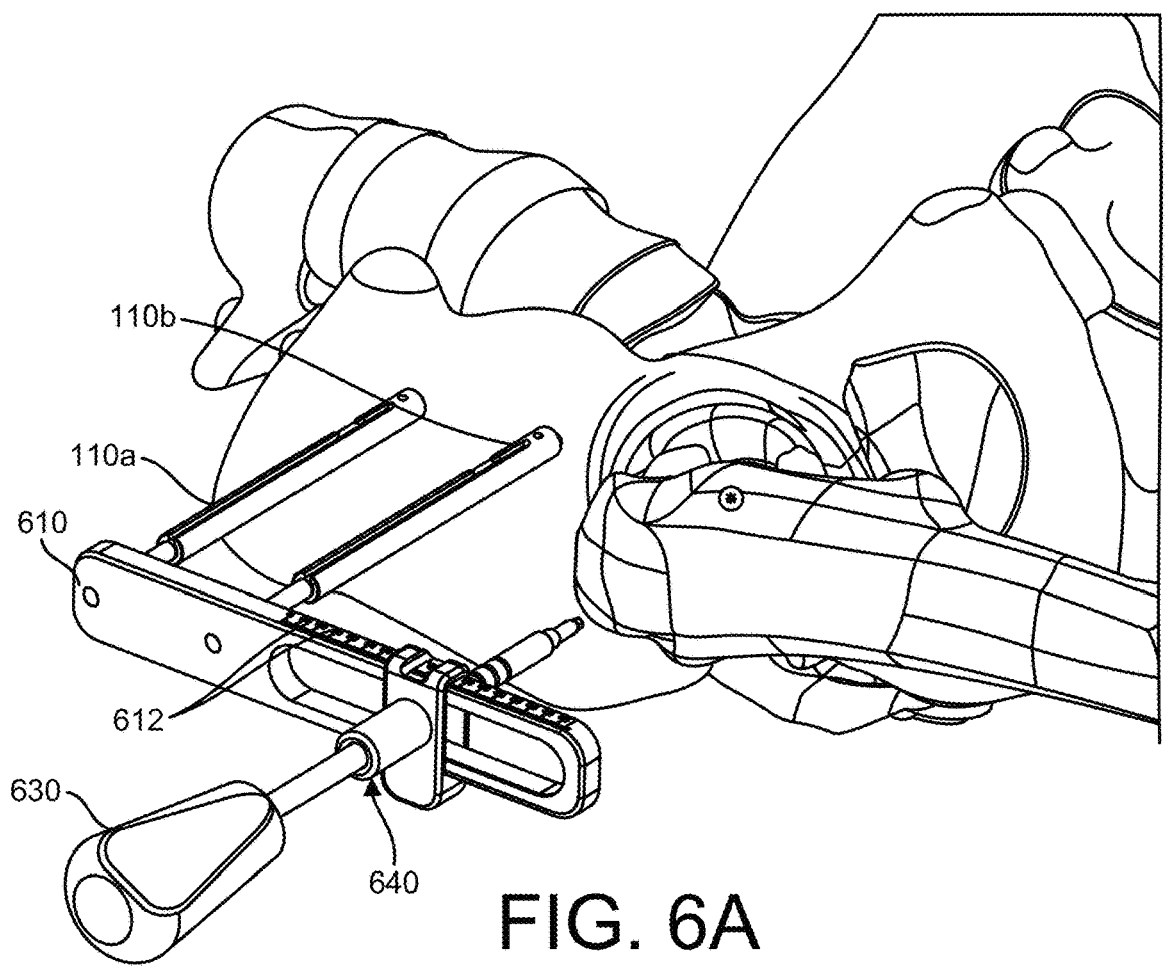
Figure 6B:
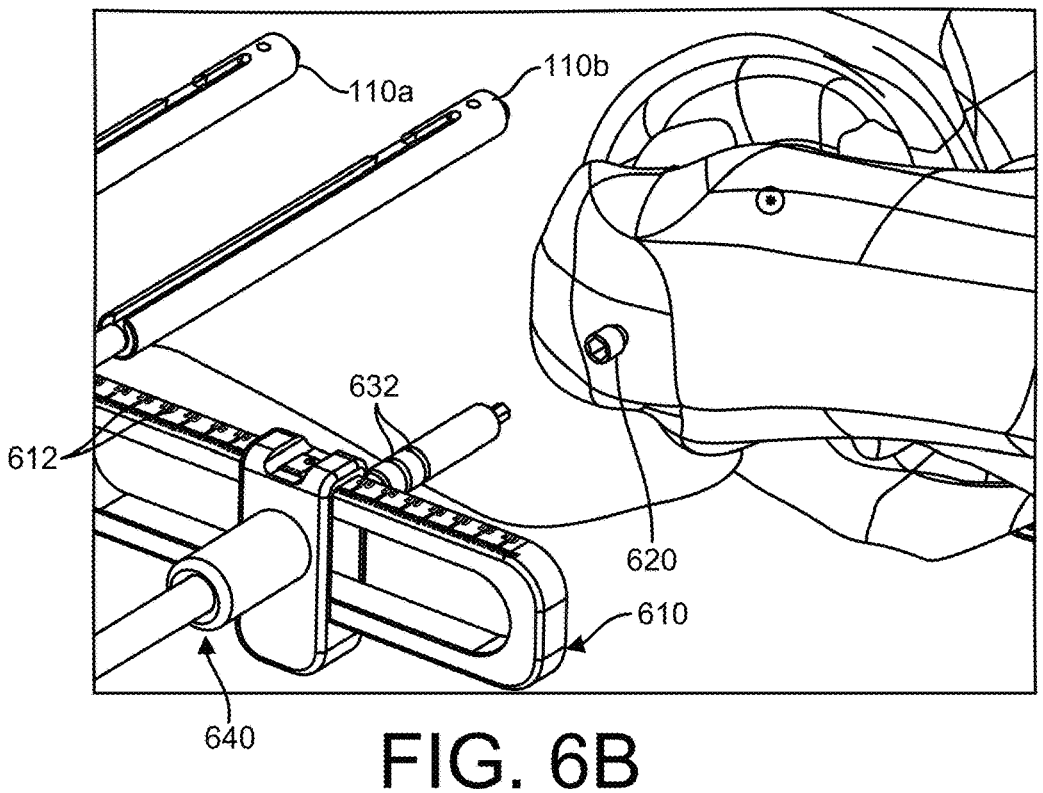

With reference to FIGS. 6A and 6B, after exposing the hip but prior to hip dislocation, a guide 610 is associated with both pins 110a,110b, to define an axis that extends over the greater trochanter. With the operative limb positioned generally along the axis of the guide 610 and maintained in neutral abduction/adduction, a screw 620 with deeply recessed hex form or similar channel for association with a screw driver 630 is advanced through a sliding drill/screw guide channel 640 associated with and orthogonal to the guide axis and generally parallel to the two pelvic pins/screws 110a,110b. The axial distance between the trochanteric reference screw 620 and the lower pelvic pin/screw 110b (or a surrogate distance) is noted from graduations 612 on the guide 610. This value is used for comparison to subsequent measurements to determine limb length changes. Additionally, the depth from an axis of the guide 610 to the screw head 620 is measured using graduations 632 on the screw driver shaft. This value can be used for assessing changes in the "hip offset", following implant trialing or implantation.

Figure 7A:
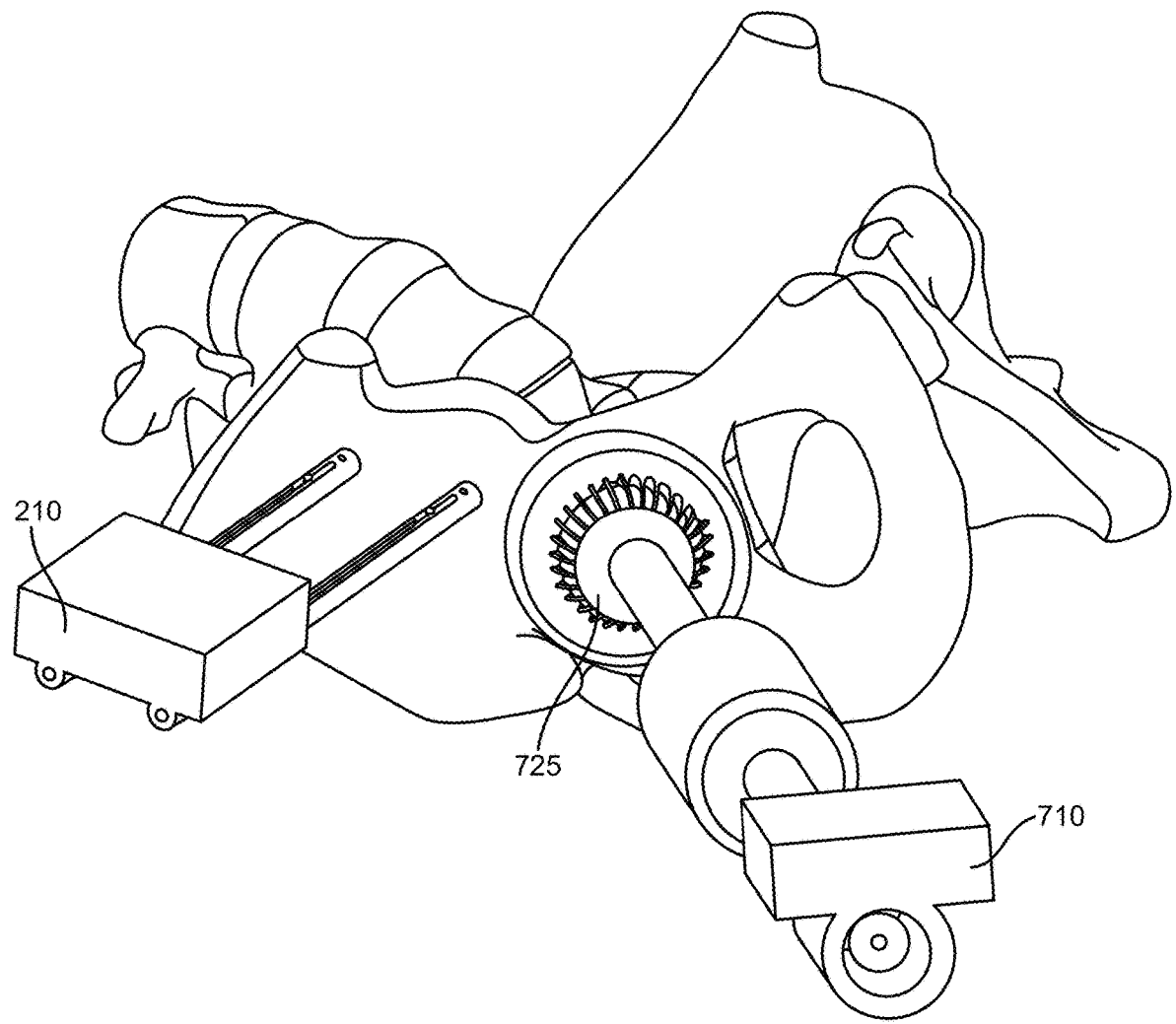
Figure 7B:
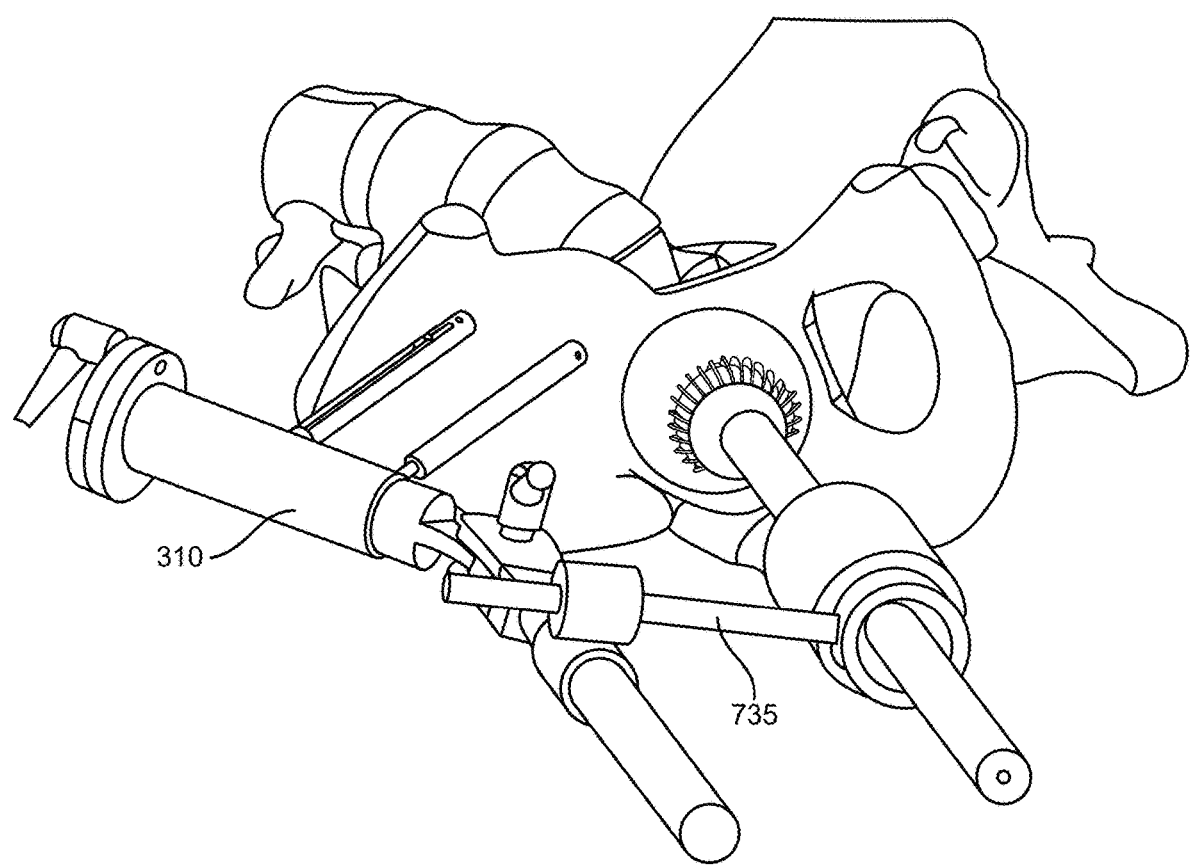
Figure 7C:
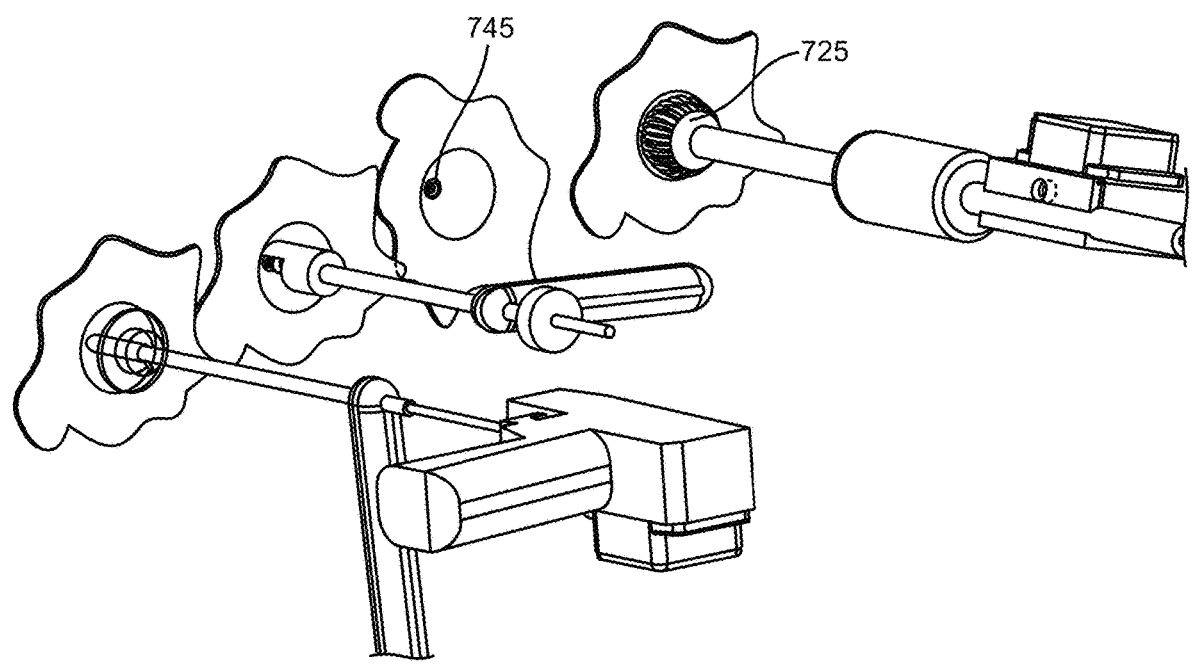
Figure 7D:
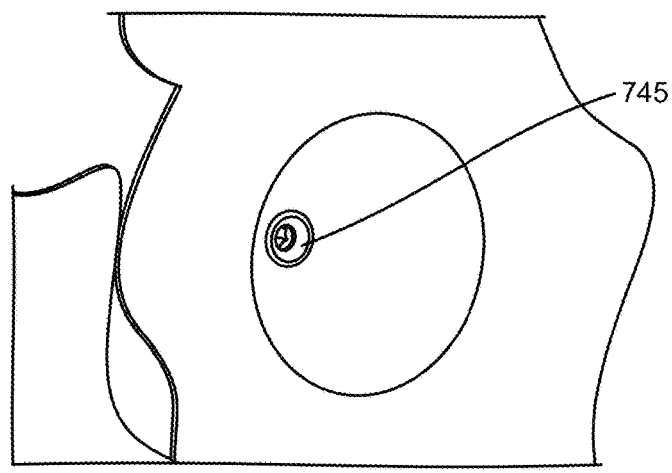

After this is completed, the guide 610 is removed and the hip is dislocated and fully prepared for acetabular reaming. With reference to FIGS. 7A-7D, the sterile wireless multi-axial reference sensor 210 (FIG. 7A) or mechanical drill guide 310 (FIG. 7B) is then secured to the two pins/screws 110a,110b in the pelvis 100 (e.g., with the aid of a thread-form that engages either an internal or external feature of the pins/screws). As shown in FIG. 7A, a second measurement sterile wireless multiaxial sensor 710 can be fixed to the acetabular floor drill or drill guide, final reaming shafts or reamer, and acetabular cup positioner, should drilling and reaming orientation relative to the pelvis be desired and the mechanical axis guide is not employed. A acetabular cup 725 is positioned with the aid of a measurement multiaxial sensor 220 to achieve optimal acetabular abduction and anteversion. Alternatively, as shown in FIG. 7B, a guide rod 735 can be oriented via the mechanical guide 310 (associated with the pins/screws 110a,110b in the hemi pelvis) and fixed to the operative table via an adjustable positioner and to the pelvis via a foveal or cotyledon notch/pelvic floor screw 745. The pelvic floor screw 745 is inserted into a pre-drilled hole in the floor of the acetabulum that is drilled in alignment with the intended reaming/implant axis (i.e., intended final inclination and anteversion). Based upon preoperative and intraoperative planning the "flat head" of acetabular floor screw 745 is positioned at a prescribed depth to control reaming depth. A central recess in the screw head accommodates the reamer guide rod/pin and implant insertion guide rod to constrain both reaming and implant insertion along a predetermined optimized axis. In accordance with an embodiment, the acetabular floor may be "spot faced" to a specific depth, such that the acetabular floor screw head, when inserted to the depth of the spot faced acetabular surface, prevents excessive acetabular floor reaming by serving as a mechanical stop to cannulated reamers. Markings on the reamer and insertion guide rod (visible above the cannulated reamer and cannulated implant insertor) provide additional visual confirmation of depth of acetabular reaming and implant insertion.

Figure 8:
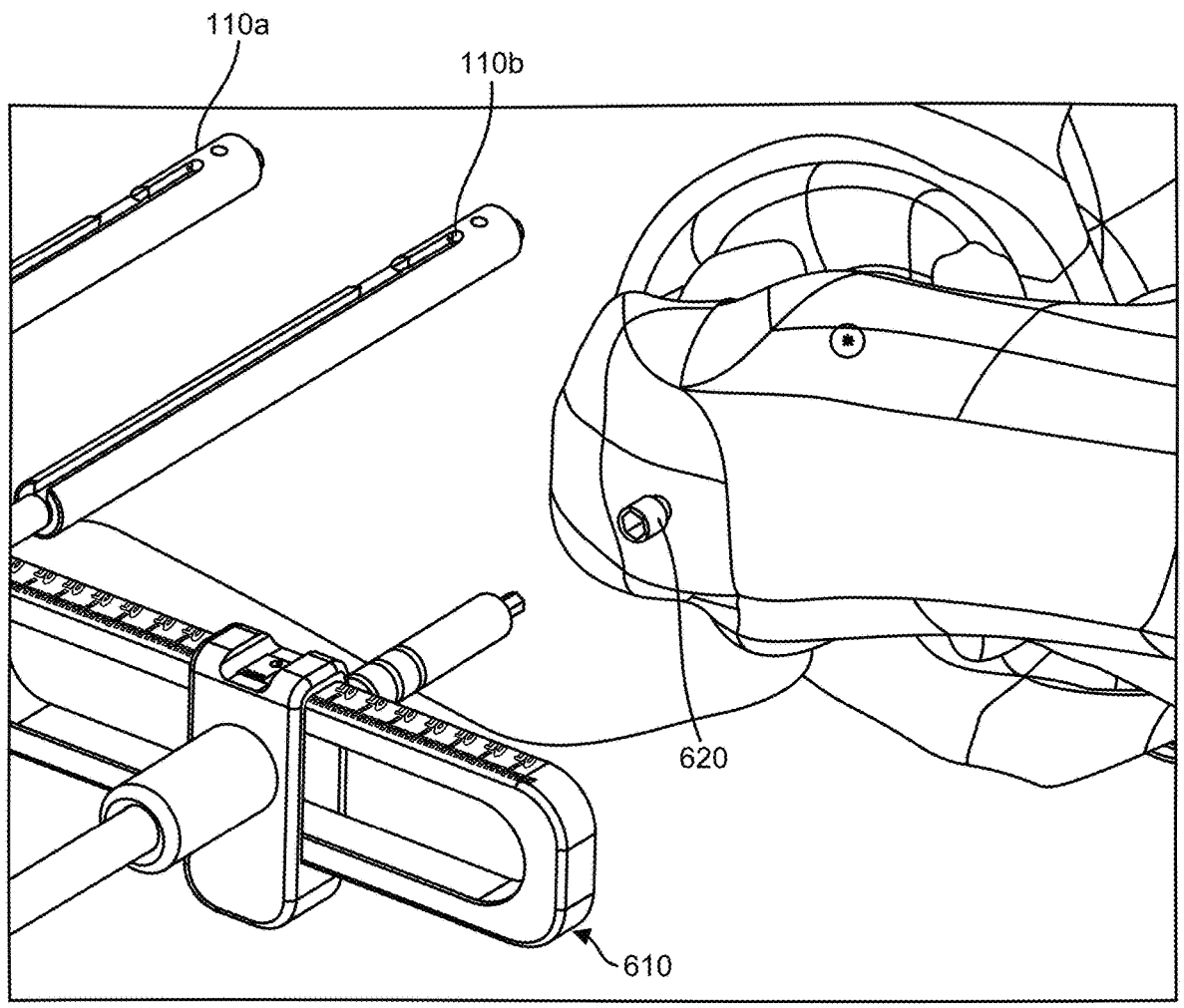

Trialing of the femoral component located within the acetabular socket with the use of the axial guide 610, and screw driver inserter associated with the previously inserted trochanteric screw 620, as shown in FIG. 8, allows for comparison and adjustment of anticipated limb length and "hip offset" (as long as the limb is returned to neutral abduction/adduction).

A method of securing the wireless reference sensor (as well as the leg length and acetabular offset measuring instruments) to the pelvis is now described. Use of relatively conventional trocar tipped Steinman pins or bone screws of various types can be used, but a more predictable means of rapidly and securely fixating to both the outer and inner tables of the pelvis, percutaneously is also disclosed.

Figure 9:
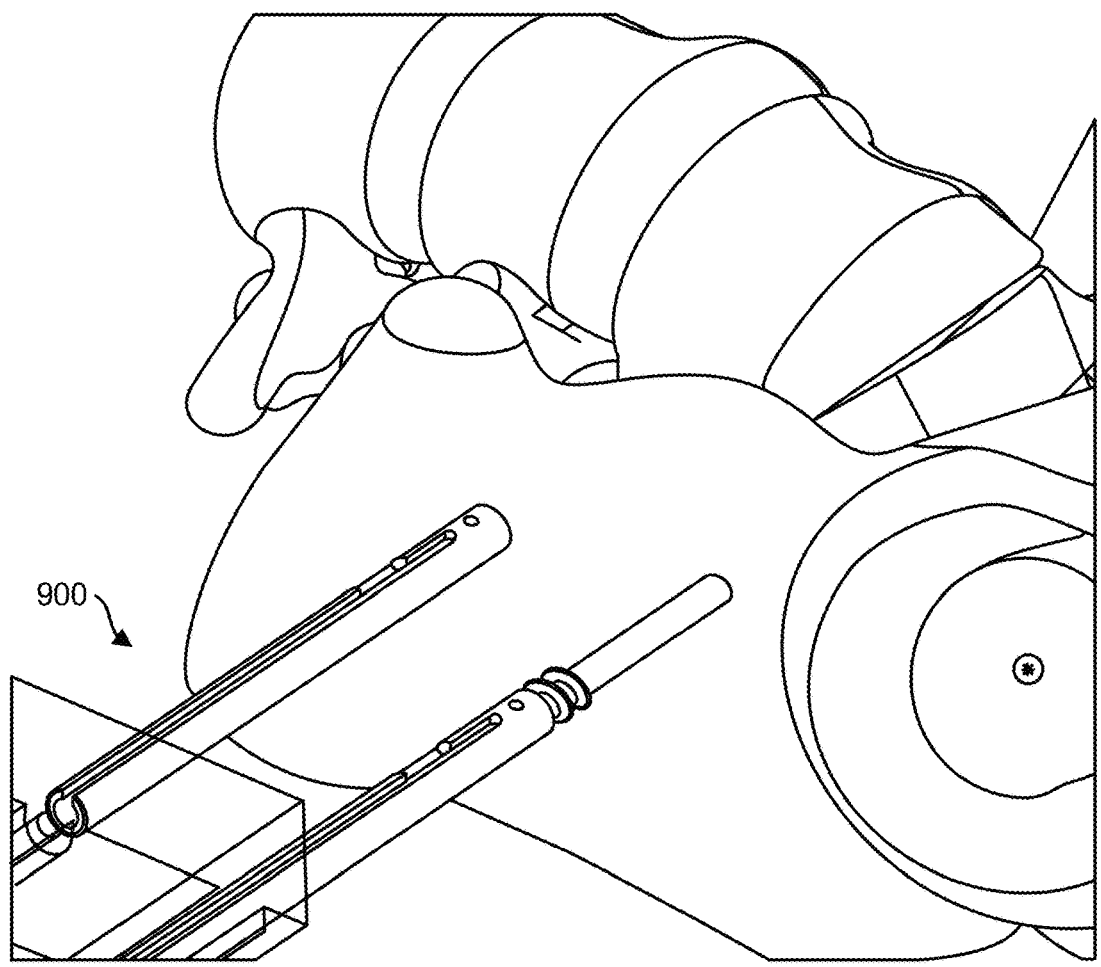
FIGS. 9-12 illustrate features of pin/screw assemblies that can be used with various implementations of the current subject matter.
Figure 10:
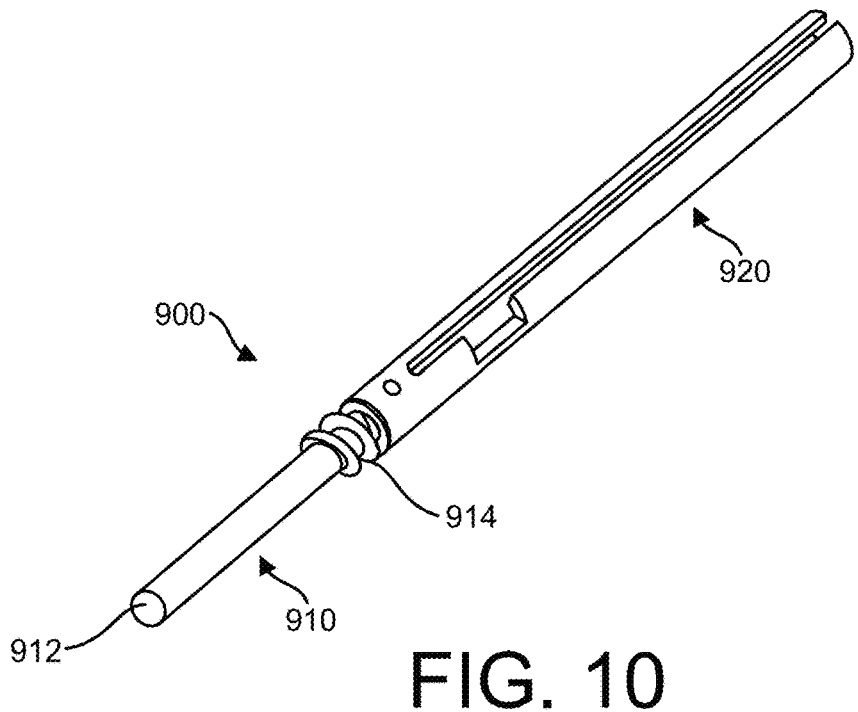
Figure 11:
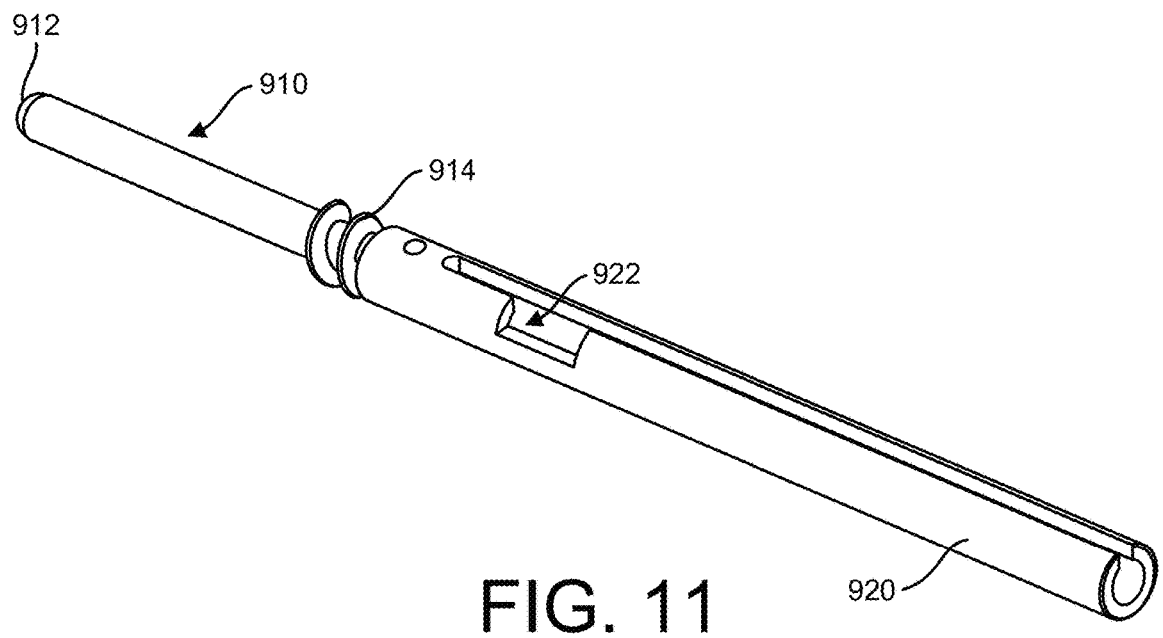

The pin-screw assembly 900 described below is an alternative to conventional pins or screw forms. The segmented pelvic pin and screw combination 900 is shown in FIGS. 9-11 in various disassembled and assembled or engaged forms. The assembly 900 includes a distal segment 910 having a piercing tip 912 as well as having a trailing or proximal external male thread form 914 and either an internal (shown in this illustrated example) or external geometric (e.g. hex, square, and Torx) form for forward advancement (driving) and rotating the combined assembly.

A proximal segment 920 of the pin-screw assembly 900 includes a cannulated element 922 having an internal (female) thread form (to compliment the male thread form 914 of the distal pin component) and an external bone thread having an identical thread pitch. In addition, the proximal component 920 has a torsional drive feature, such as the external hex drive feature shown.

A cannulated torsion drive can be used to advance the proximal threaded segment 920 on to the distal pin segment 910, while the pin handle is utilized to provide counter rotational resistance to the pin.

Figure 12:
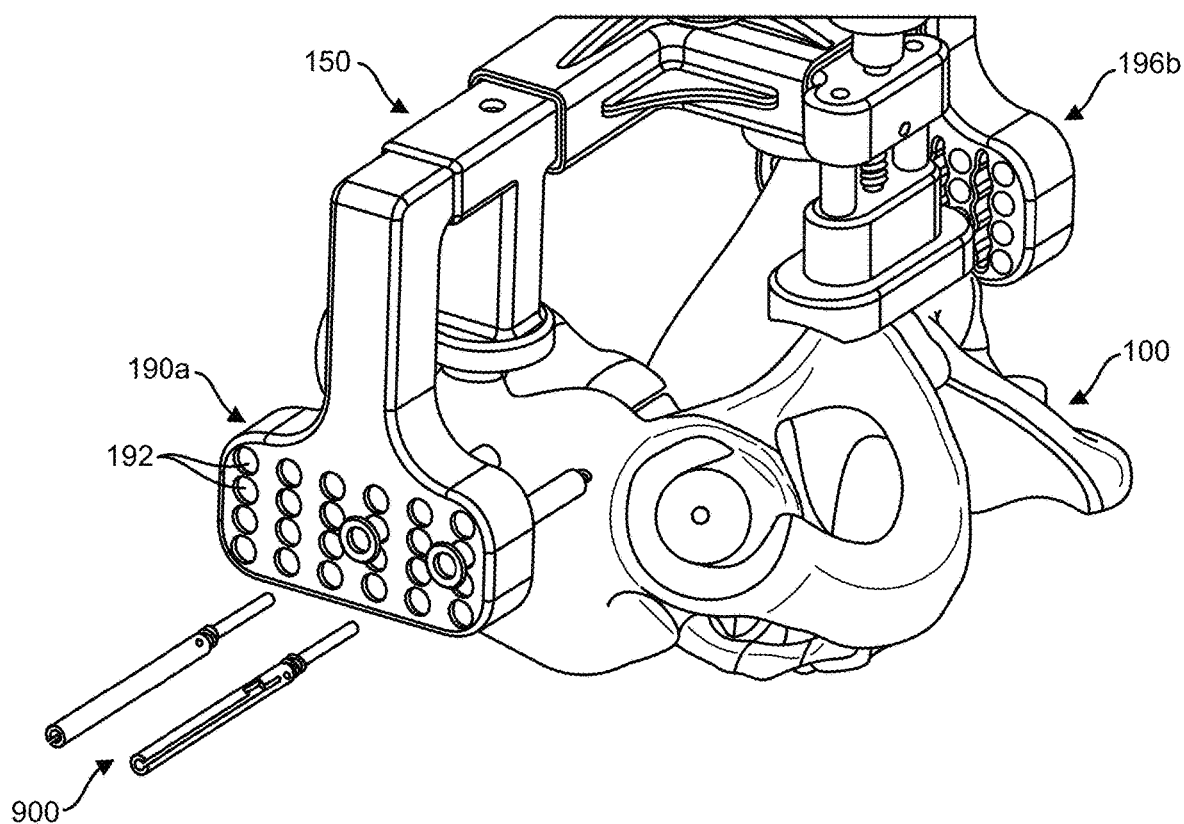

With reference to FIG. 12, a mechanism of securing the pin-screw assembly 900 to the pelvis 100 can be used. The surgeon advances the pin-screw assembly 900 through one of the guides 192 provided by the pelvic navigation frame 150 (either through a percutaneously placed cannula within the soft tissue or directly through the soft-tissue envelope) directly to the outer surface of the hemipelvis. Striking the back of the pin driver handle with a mallet (with or without rotation of the handle), the pin screw assembly 900 (in state in which the externally threaded screw component is only partially threaded onto the distal pin segment) is advanced through the outer pelvic table and either into or through the inner table.

Once the pin is advanced to the depth of the inner table, the pin handle is held securely (resisting transmitted rotational loading of the pin) while the threaded segment is advanced over the pin with the rotation of its associated cannulated insertion instrument handle. Once the threaded segment of the assembly is fully thread engaged onto the distal pin segment of the assembly, the handles are removed and the pin-screw assembly is subsequently utilized for positioning posts within the features of the cannulated screw segment for various measurement purposes (e.g. multiaxial reference sensor, leg length and trochanteric off-set measuring instrument).

Interference fit of various means between the drivers and assembly components are anticipated, including friction fit, slotting of either the driver or driven component for collapsing and/or splaying of either to increase the dissociation force required to separate driver from driven component.

FIGS. 13-30 illustrate features of an alternate embodiment that employs an adjustable reamer and implant insertion guide that is mounted to two or more pins fixed to the pelvis to guide acetabular reaming and acetabular implant insertion. This employs an electronic level that can be substituted for a leveling rod to indicate the angle of the pelvic frame. This allows the user to compare the angle of the pelvic reference frame to the observed and measured inclination of the anterior pelvic plane, as viewed on a lateral X-ray (preoperatively or intraoperatively). Thus, the frame can be adjusted to reproduce that same angle and thus compensate for soft tissue disparities under the supporting stanchions.

Figure 13:
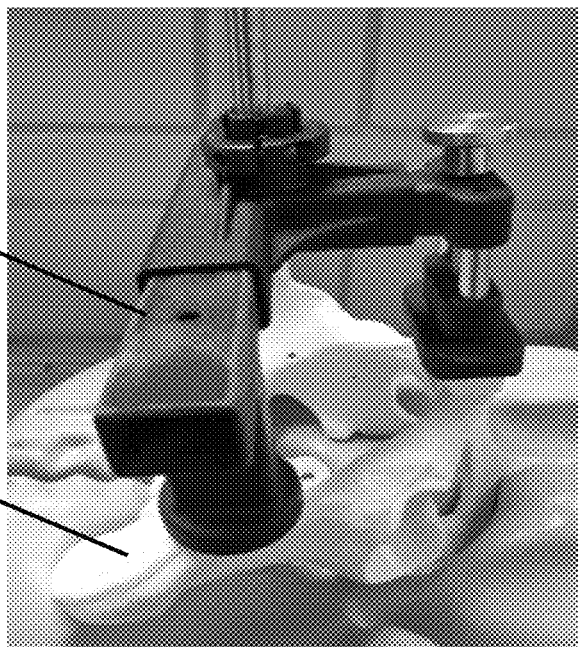
FIGS. 13-29 illustrate features of an alternate embodiment.
Figure 14:
Figure 15:
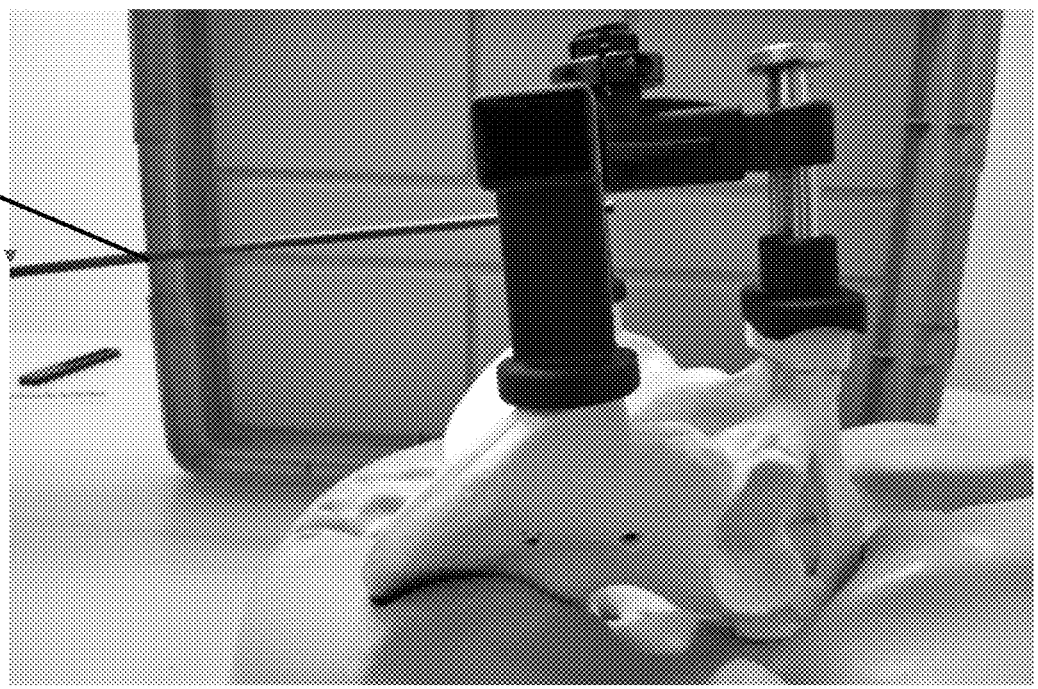

FIG. 13 shows the frame 150 mounted on a pelvis 100. FIG. 14 shows the frame 150 compressed and secured to a table rail. As shown in FIG. 15, a leveling rod is then coupled to the frame and then the leveling rod can be manually adjusted, as shown in FIG. 16.

Figure 16:
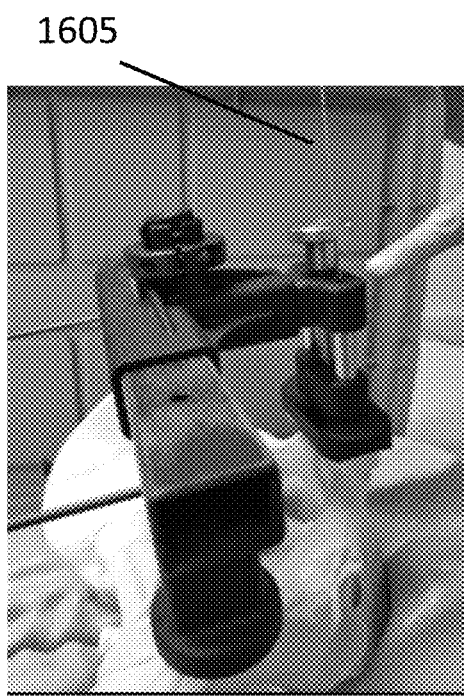
Figure 17:
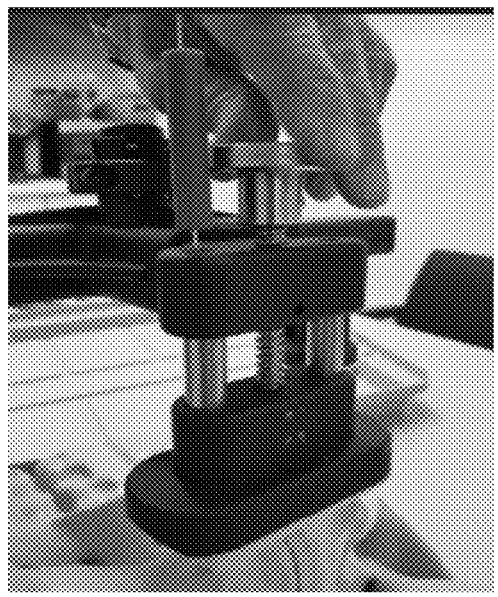
Figure 18:
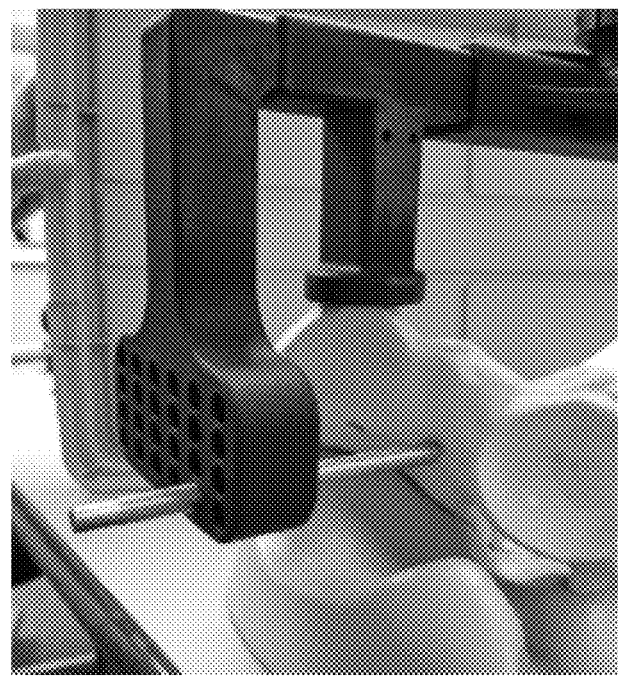

With reference to FIG. 16, a pin (such as an 18 gauge tapered tip pin) is inserted through the frame and soft tissue to the superficial cortex. The pin is used for soft tissue probing to the ASIS. The pin can include an indicator that shows a disparity of soft tissue depth. A pubic tubercle stanchion is then lowered to equalize the height of the soft tissue depth gauge (FIG. 17) and obturator or cannula is placed through the frame above the operative acetabulum (FIG. 18).

Figure 19:
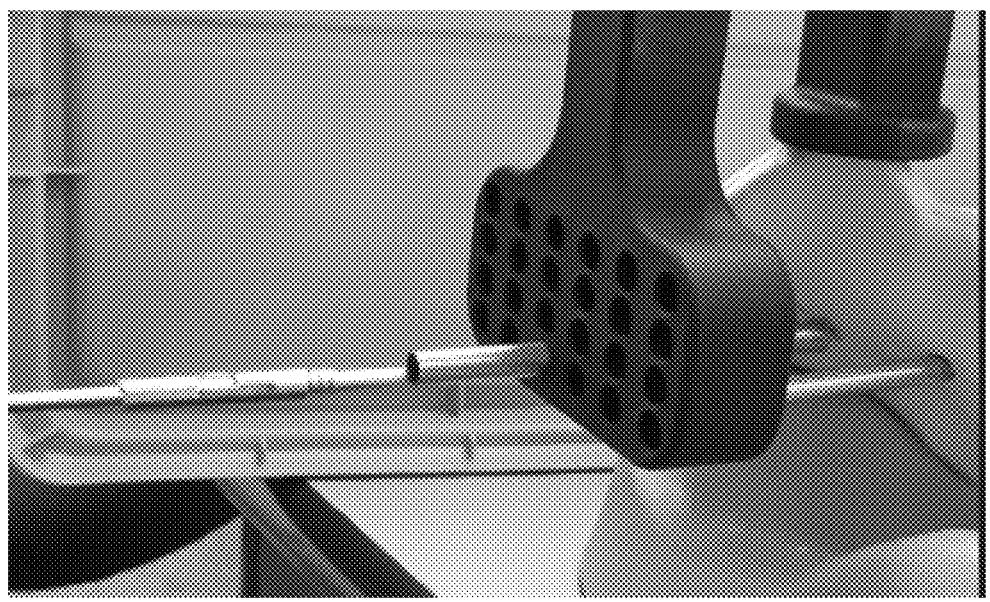

Percutaneous bicortical drilling of the ilium is then performed along with percutaneous insertion of a distal blunt threaded reference pin. A second pelvic reference pin is then inserted so that the two pins are parallel to one another, as shown in FIG. 19. The pins define a plane that is parallel to the plane with which the pelvic frame has been aligned (e.g. anterior pelvic plane or coronal plane).

Figure 20:
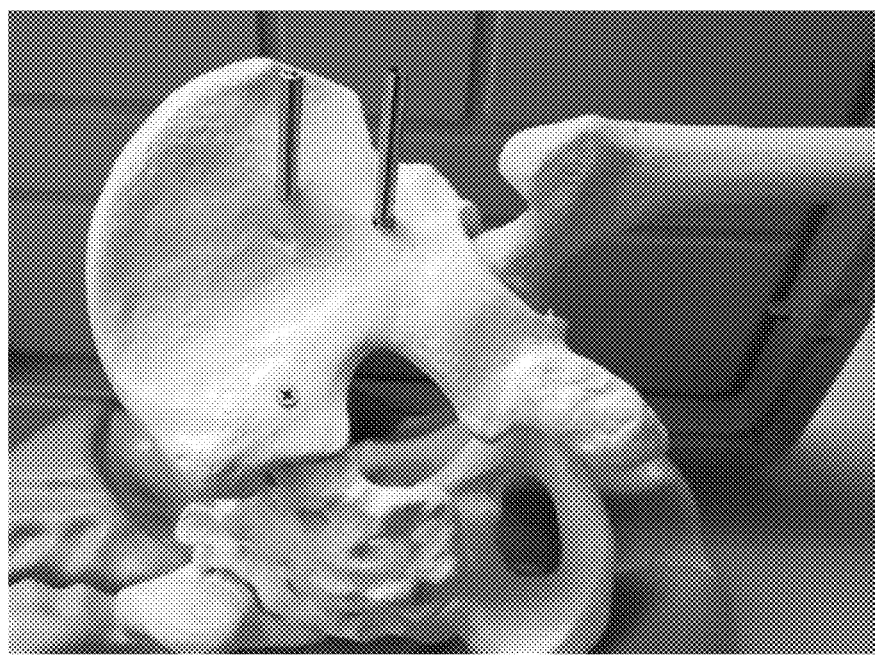
Figure 21:
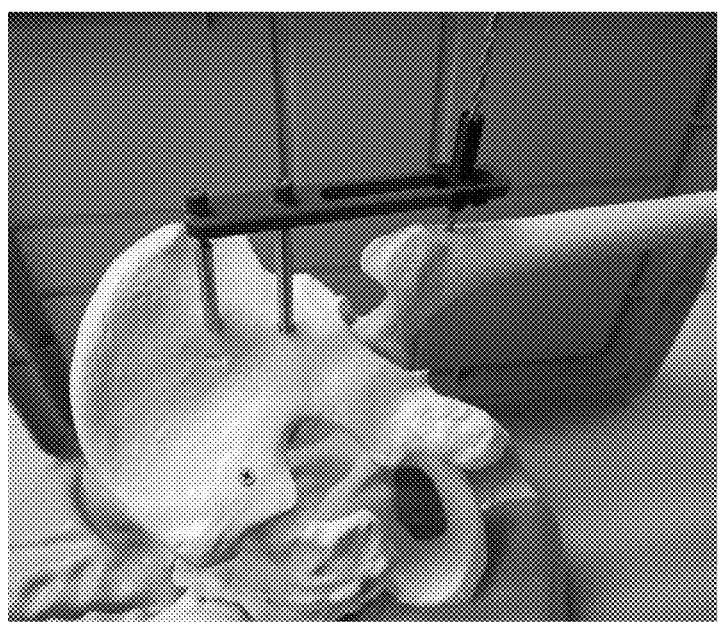
Figure 22:
Figure 23:
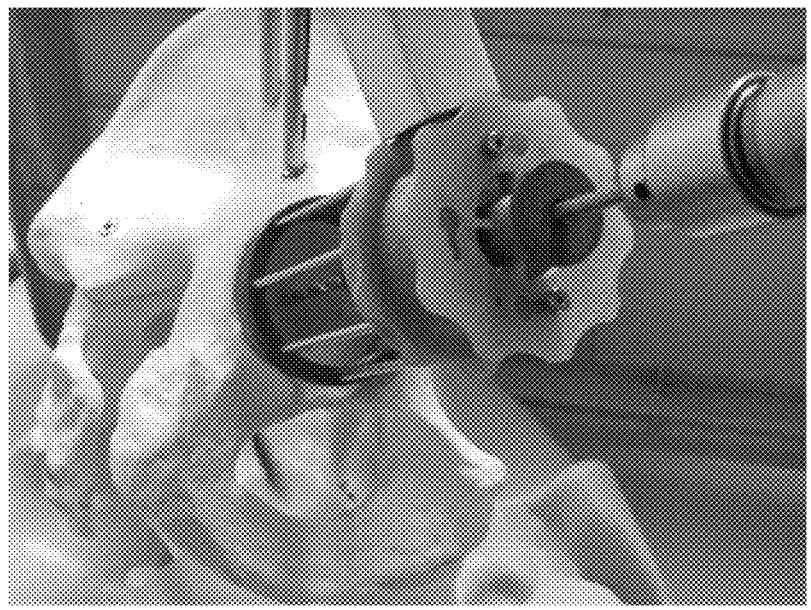

FIG. 20 shows the pelvis in the lateral decubitus position with the pelvic reference pins extended to skin level. A drill is then placed through a drill guide associated with the limb length and the trochanteric offset indicator, as shown in FIG. 21. A reference screw is then inserted in the proximal femur. With reference to FIG. 22, an inclination and anteversion guide is positioned into the pelvic reference pins and a hemisphere component is positioned within acetabulum and then associated with the acetabular jig to drill at the desired axis of inclination. FIG. 23 shows co-axial drilling of the acetabular medical wall.

Figure 24:
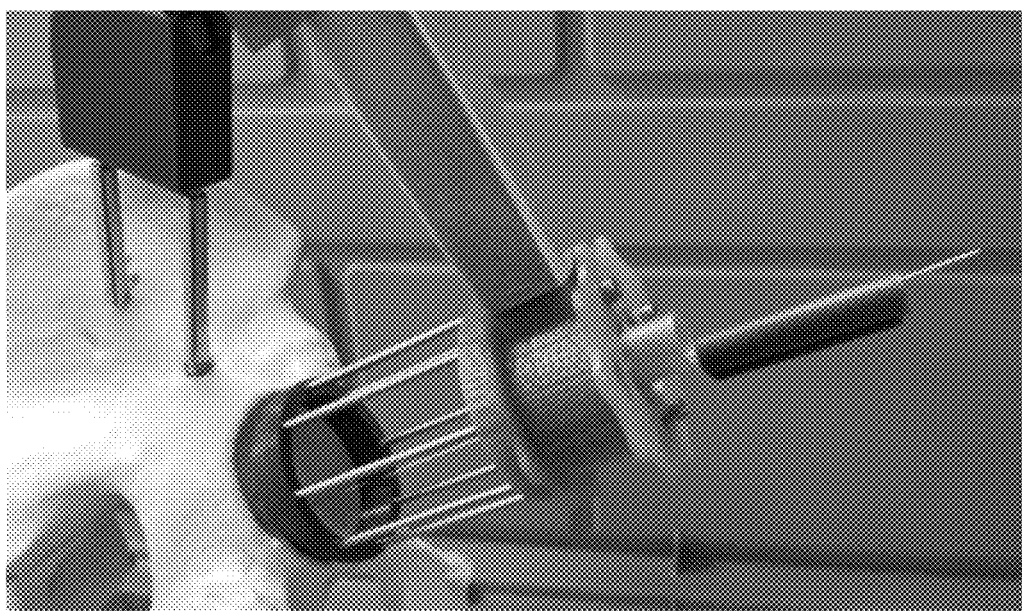
Figure 25:
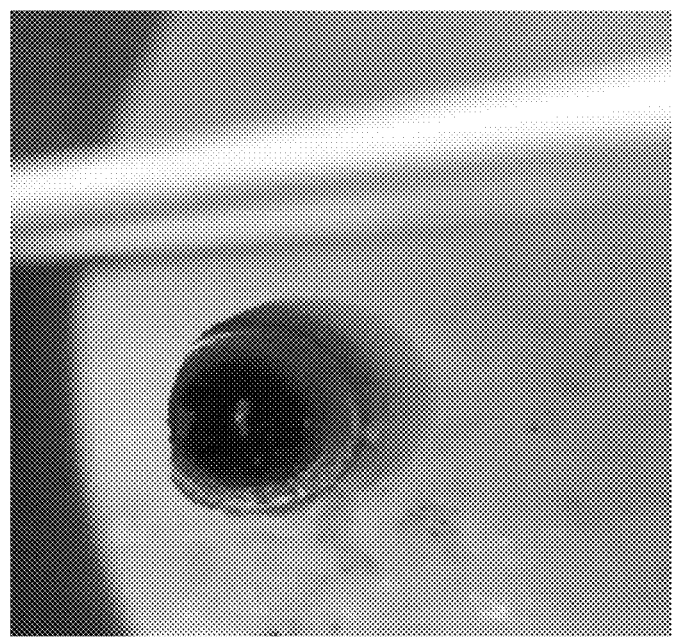
Figure 26:
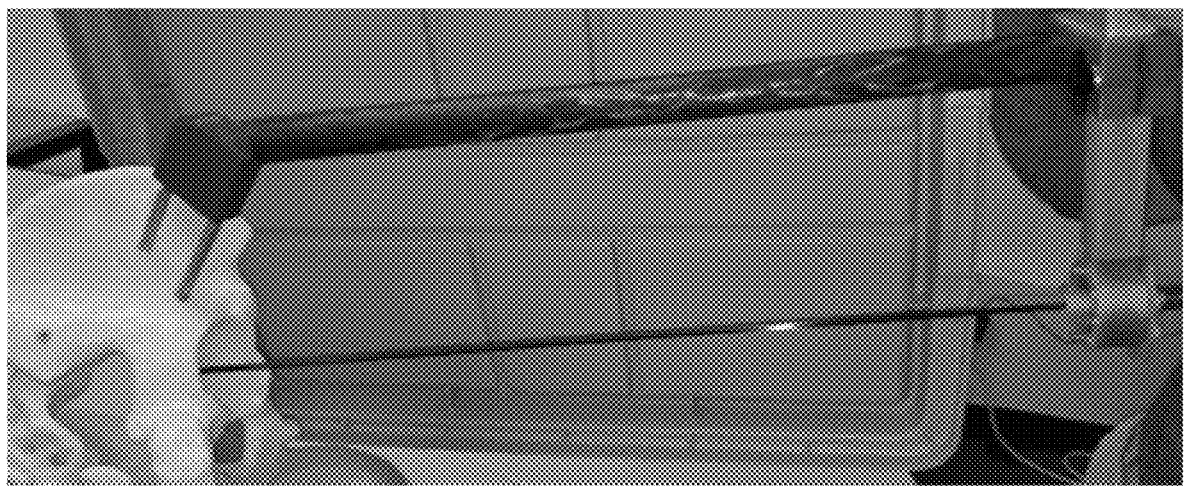

As shown in FIG. 24, a depth gauge is used to determine a distance to the acetabular floor or cotyled on notch depth. A drill and spot facer guide is used to co-axially drill and spot face and the acetabular floor guide and reamer depth stop screw is inserted until fully seated, as shown in FIG. 25. A reamer and implant insertion guide rod (such as a 4 mm carbon fiber composite rod) is then seated in the reamer guide. FIG. 26 shows the reamer guide with the guide pin supported both medially and laterally. The reamer guide can be used with the pin supported both medially and laterally and with a cannulated reamer shaft and head positioned over the guide pin.

Figure 27:
Figure 28:
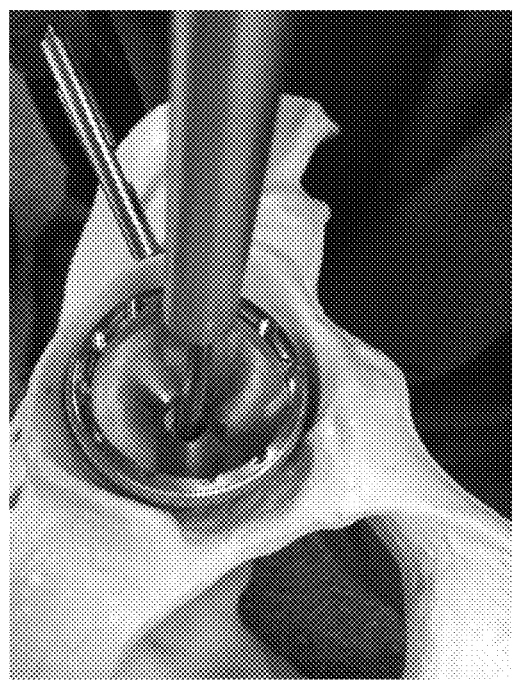
Figure 29:

In FIG. 27, a cannulated acetabular reaming with guide pin and axial orientation assembly is shown. An acetabular implant is inserted over the large diameter guide pin using a cannulated driver, as shown in FIG. 28. The implant is then seated coaxial with the reaming axis, as shown in FIG. 29. This can be controlled with a medial acetabular screw as well as corresponding visual markings on a 4 mm reamer guide shaft and a 6 to 7 implant driver guide shaft. Once the acetabulum has been reamed, the implant is inserted along the same axis using a large guide pin (such as 6-7 mm). The medial acetabular guide and depth stop screw is then removed from the acetabulum through the acetabular shell's central aperture.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

We claim:

1. A method for aligning a surgical intervention in a skeletal structure, the method comprising:
mounting a three-legged frame relative to a pelvis of a patient with a first leg and a second leg resting on a respective cutaneous surface immediately superficial to anterior superior iliac spine (ASIS) prominences and a third leg supported by subcutaneous tissue immediately superficial to a symphysis pubis (SP);
inserting a first pin and a second pin into a hemi-pelvis of a patient via the three-legged frame, wherein the first pin and the second pin are both aligned parallel with a line defined by anterior superior iliac spine (ASIS) prominences;
attaching a first spatial sensor to the first pin and the second pin so that the spatial sensor is attached to the skeletal structure;
positioning a second sensor relative to the first spatial sensor, the second sensor configured to spatially reference the first spatial sensor to allow for surgical intervention in the skeletal structure along at least one prescribed axis spatially oriented relative to the skeletal structure.

2. The method of claim 1, wherein the first spatial sensor and the second sensor comprise multiaxial sensors.

3. The method of claim 2, wherein the multiaxial sensors comprise at least one inclinometer.

4. The method of claim 2, wherein the multiaxial sensors comprise at least a compass or magnetic pole directional indicator.

5. The method of claim 1, wherein the first spatial sensor and the second sensor communicate via a wireless connection.

6. The method of claim 1, further comprising determining a limb length by utilizing an adjustable surgical guide fixed to the one or more pins and measuring a distance from a third pin fixed to a greater trochanter of the patient.

7. The method of claim 6, wherein the adjustable surgical guide comprises graduations for the measuring.

8. The method of claim 1, wherein the first pin and the second pin are parallel to a plane that contains two anterior superior iliac spine (ASIS) prominences.

9. The method of claim 1, further comprising determining reference abduction and anteversion values using the first spatial sensor.

10. The method of claim 1, wherein the frame includes a surgical guide having at least one guide channel through which the first pin and the second pin are inserted.

11. The method of claim 10, wherein the surgical guides position the first pin and the second pin in the lateral pelvis superior to the acetabular cavity.

12. A method for aligning a surgical intervention in a skeletal structure, the method comprising:
[mounting a three-legged frame relative to a pelvis of a patient with a first leg and a second leg resting on a respective cutaneous surface immediately superficial to anterior superior ilia spine (ASIS) prominences and a third leg supported by subcutaneous tissue immediately superficial to a symphysis pubis (SP);] placing a first pin and a second pin in a hemi-pelvis of a patient [via the three-legged frame], wherein a first spatial sensor is coupled to the first pin and a second spatial sensor is coupled to the second pin;
mounting a guide frame to the hemi-pelvis using the first pin and the second pin;
orienting a hip implant relative to the hemi-pelvis using the guide frame;
determining a limb length by utilizing the guide frame.

* * * * *